(12) United States Patent
Tavares

(10) Patent No.: US 6,506,712 B2
(45) Date of Patent: Jan. 14, 2003

(54) METHOD OF MANUFACTURING A MULTIFUNCTIONAL ADDITIVE AND USING THE SAME

(75) Inventor: Bruce A. Tavares, Blairstown, NJ (US)

(73) Assignee: React, LLC, Delafield, WI (US)

( * ) Notice: Subject to any disclaimer, the term of this patent is extended or adjusted under 35 U.S.C. 154(b) by 0 days.

(21) Appl. No.: 09/861,842

(22) Filed: May 21, 2001

(65) Prior Publication Data

US 2002/0173432 A1 Nov. 21, 2002

(51) Int. Cl.[7] ...................... C10M 159/00; C08B 11/20
(52) U.S. Cl. .................. 508/216; 8/116.1; 204/157.15; 204/157.63; 204/157.68; 536/85
(58) Field of Search ................................. 508/216, 219

(56) References Cited

U.S. PATENT DOCUMENTS

| | | | |
|---|---|---|---|
| 3,108,890 A | 10/1963 | Beaver et al. ......... | 204/157.63 |
| 3,502,426 A | 3/1970 | Krassig et al. ............... | 8/116.1 |
| 3,846,521 A | 11/1974 | Osterholtz ................... | 264/22 |
| 3,962,054 A | 6/1976 | Wattiez et al. ......... | 204/159.12 |
| 4,051,306 A | 9/1977 | Tobias et al. .................. | 526/1 |
| 4,190,623 A | 2/1980 | Bobeth et al. ................. | 264/22 |
| 4,316,982 A | 2/1982 | Holst et al. ................... | 536/88 |
| 4,486,585 A | 12/1984 | Turunen et al. ................ | 536/30 |
| 4,654,379 A | 3/1987 | Lapin ........................... | 522/15 |
| 5,505,830 A * | 4/1996 | Petcavich .............. | 204/157.63 |
| 5,710,274 A | 1/1998 | Yuan et al. .................. | 544/375 |
| 5,719,274 A | 2/1998 | Doenges et al. .............. | 536/85 |
| 5,928,709 A | 7/1999 | Doenges et al. ........... | 427/2.14 |
| 6,124,248 A * | 9/2000 | O'Bryant et al. ........... | 508/216 |
| 6,320,042 B1 * | 11/2001 | Michihata et al. ............ | 536/69 |

OTHER PUBLICATIONS

"Electron Processing Technology: A Promising Application for the Viscose Industry" presented at the 10th International Meeting on radiation Processing, May 11–16, 1997, Anaheim, CA.

* cited by examiner

*Primary Examiner*—Ellen M. McAvoy
(74) *Attorney, Agent, or Firm*—Andrus, Sceales, Starke & Sawall, LLP

(57) ABSTRACT

Additives useful for reducing the coefficient of friction in lubricants, greases, or cosmetic formulations, and useful as a substitute for talc and as an anti-misting material are obtained by subjecting a raw plant material, such as cotton, to a dosage of radiation from an electron beam source. The irradiated plant material is subsequently fragmented, or micronized, to product the friction-reducing additive with a reduced diameter capable of reducing the coefficient of friction, used for anti-misting or as a substitute for talc in a variety of applications.

18 Claims, No Drawings

METHOD OF MANUFACTURING A MULTIFUNCTIONAL ADDITIVE AND USING THE SAME

FIELD OF THE INVENTION

The present invention relates to multifunctional additives and methods for preparing and using the same. Specifically, multifunctional additives are produced by irradiating and subsequently fragmenting, or micronizing, plant materials, such as raw cotton. A multifunctional additive made in accordance with the method of the present invention has the following attributes: (1) anti-misting properties, (2) low coefficient of friction, (3) is suitable for use as a substitute for talc, as for example in cosmetics and other personal care products, and (4) is suitable as a substitute for asbestos in coating applications.

BACKGROUND OF THE INVENTION

Radiation processing for modification and enhancement of polymeric material properties has been well documented in the prior art. In particular, electron beam processing has been used to improve thermal, chemical, barrier, impact, wear, and other properties of many inexpensive materials extending their utility to demanding applications typically dominated by higher cost materials. Electron beam processing may result in cross-linking, degradation, or a combination of the two, depending on the nature of the polymeric materials and the dosage of radiation applied. Results of electron beam processing of cross-linkable plastics has yielded materials with improved dimensional stability, reduced stress cracking, higher service temperatures, reduced solvent and water permeability. More specifically, radiation induced cross-linking in polyethylene has resulted in increased modulus, tensile and impact strength, hardness, deflection and service temperature stress/crack resistance, abrasion resistance, creep and fatigue resistance. In contrast, radiation processing can also induce degradative, or scissioning, effects in polymeric materials such as polytetrafluoroethylene (PTFE). Scrap or off-spec PTFE, degraded by electron beam processing, has been identified as useful in the production of abrasion-reducing additives.

PTFE has found a use as a friction-reducing additive in many areas, including the printing ink industry. PTFE additives provide ink formulations with anti-rub properties so that the inks are resistant to smearing and marring. However, PTFE cost is relatively high in comparison to other anti-abrasion additives and therefore PTFE use is often cost prohibitive.

Radiation processing has also been used in degrading high molecular weight cellulose ethers common polymeric materials into low molecular weight cellulose ethers producing low molecular weight cellulose ethers for varying uses. For example, U.S. Pat. No. 5,928,709 to Doenges et al. discloses a method of producing low molecular weight cellulose ethers by irradiation of a mixture of higher molecular weight cellulose ethers and an Arrhenius and/or Bronsted base. The resulting low molecular weight cellulose ethers are suitable as water-binding agents, thickeners and emulsion stabilizes.

Clays and talcs have also found traditional use in the reduction of friction. For instance, clays are currently used in down hole drilling fluids useful in reducing friction during drilling operations. Debris present in a down hole is cleared by pumping clay into the bore hole where the clay lowers the viscosity of the debris and aids in moving the clay to an exit. Ideally, the clay maintains the debris in a suspended mixture without building viscosity. In practice, a significant buildup in viscosity is experienced in this process and the efficiency of clearing debris from down holes using clay is significantly less than desired. The cost of suitable clays may also be prohibitive.

Talc has found wide use as a friction-reducer in personal care products, most notably mascaras and body powders. Although hypoallergenic in nature and therefore safe for contact with the human body, talc suitable for personal care products is expensive to manufacture.

The above-described background highlights the need for multifunctional additives with improved low COF characteristics obtainable at a reduced cost. Such additives should not only be economical to manufacture, but also derived from a cheap but plentiful raw material source. The method of manufacture should also be flexible to accommodate production of additives suitable for a variety of applications.

SUMMARY OF THE INVENTION

The invention relates to a method for preparing a multifunctional additive from a raw plant material and, in particular, cotton. The raw plant material is irradiated with an electron beam source to form an irradiated product. During the irradiation, the raw plant material is continually blended to provide a uniform radiation dosage to the raw plant material. Following irradiation, the irradiated product is fragmented, or micronized, to form the additive having an average diameter size less than that of the original raw plant material starting product.

In the preferred embodiment of the invention, the method utilizes raw cotton as the raw plant material.

Prior to the irradiating step of the invention, a granulating step may be included wherein the raw plant material is granulated to reduce the diameter size of the raw plant material before irradiating. In one approach to the invention, the granulating step may reduce the raw plant material to about a ⅛ inch to about a ¼ inch diameter size prior to the irradiating step.

The irradiation step of the invention utilizes an electron beam source for delivering accelerated electrons to the raw plant material. A suitable dosage may be between about 30 megaRads to about 100 megaRads depending upon the particular application the resulting additive will be used in. A dosage of about 80 megaRads to about 100 megaRads is preferable where the additive will be used in friction-reducing applications. However, the total dosage is preferably administered in multiple low dosage passes.

The micronizing step of the invention is meant to reduce the size of the irradiated product and may be carried out with a jet classifying mill. The micronizing step is intended to reduce the average diameter size of the irradiated plant material to an average diameter size of about 3 microns to 4 microns with 99% of the average diameter sizes being below 10 microns.

In addition to a preparatory method, the invention is also directed to an additive, useful in reducing friction, providing anti-misting properties, and suitable as a substitute for talc and asbestos, produced from a raw plant material having been subjected to irradiation by an electron beam. During irradiation, the raw plant material is continually blended so that the raw plant material receives a uniform dosage of irradiation. The irradiated product is subsequently micronized to form an additive with a reduced diameter. The raw plant material used to product the additive is preferably raw cotton.

An additive according to the invention as described above is useful in reducing the coefficient of friction of a substance and may be mixed with the substance in a sufficient amount to effectively reduce the coefficient of friction of the substance/additive mixture. The substance may be a lubricant/grease, cosmetic formulation, or matting agent.

Various other features, objects and advantages of the invention will be made apparent from the following description taken together with the drawings.

DETAILED DESCRIPTION OF THE INVENTION

The preferable raw plant material is raw cotton, possibly brought into the process in a baled form subsequent to harvest activities. Cotton is particularly desirable because no pretreatments of starting materials are necessary and raw natural products may be brought directly from their original source (e.g., harvest from a field) into the process, therefore reducing costly pretreatment steps such as etherification.

Cotton is a particularly attractive raw plant material for the invention as cotton is grown in about 80 countries, in a band that stretches around the world between latitudes 45° N to 30° S. After planting, seedlings appear five days later, with the first flower buds appearing after approximately six weeks. In another three to five weeks, these buds become flowers. The flowers are short lived and fall from the cotton plant, leaving behind a small seed pod, known as the boll. Each boll contains about 30 seeds, and up to 500,000 fibers of cotton. Each fiber grows its full length in three weeks and for the following four to seven weeks, each fiber gets thicker as layers of cellulose build up cell walls. Approximately ten weeks after flowering, the boll splits open and the raw cotton fibers are exposed to sunlight. As the fibers lose water and die, each fiber collapses into a twisted ribbon structure. Cotton is then picked by hand or by cotton harvesters. Cotton fibers are separated from the associated cotton seeds in a process called ginning. Following ginning, the cotton fiber is pressed into bales and wrapped for protection.

Prior to processing the raw cotton through the method according to the invention, the raw cotton fibers are debated, thus allowing the cotton fibers to be stretched into a thin sheet. The unbaled cotton sheet is cut or chopped into fairly small pieces, for example, about 2"×2" in size. The cut pieces are then fed into a pelletizer or a compressor and compressed into pellets of about ½" in size. Alternately, if palletizing is not acceptable, the cut pieces may be chopped to form small squares in the range of ½" to ¼" in size. Chopping may be performed in a HOG or Cumberland chopper or similar equipment.

Thereafter, it is preferred to expose the raw cotton material to irradiation with electrons when the raw material is in a relatively dry state. Preferably, the raw material will have a water content of less than about 0.05% to 1.0% by weight of the raw material.

Various sources of radiation may be utilized with the process according to the invention. Useful sources of radiation may be either continuous or pulsed electron beam accelerators currently available in the art. In general, any accelerator from the main types including electrostatic direct-current, electrodynamic DC, radio frequency linear accelerator, magnetic-induction LINACs and continuous wave machines may be used in the process. The dosage, or amount of energy absorbed, is measured in units of mega-Rads (MR or Mrad), where one MR is equal to one million ergs per gram, or kilograys (kGy), where one kGy is equal to one thousand joules per kilogram. The energy dose delivered to the raw material in the method is 30 to 100 MR. Preferably, dosages on the high end of that spectrum, 80 to 100 MR are preferred where the resulting irradiated materials will be used as anti-friction additives.

In accordance with the presently preferred embodiment of the subject invention, the radiation is produced by an electron accelerator. The electron beam is applied through a window to the pellets or small chopped pieces of cotton being carried on a tray system where the material is blended or turned after each pass through the beam window. The irradiation and blending may also be carried out in a ribbon type blender with the radiation applied through a beam window or with a beam horn. In a typical electron accelerator, a dosage of 2.5 MR is applied per pass of the product past the beam window. If the radiation dose is higher, the cotton may burn or degrade. Thus, with a total dosage of 80 MR, the material must be passed under the accelerator window thirty-two times. After each pass, the material must be turned over or blended before again being exposed to the radiation.

In contrast, a process according to the invention avoids the limitations in prior art techniques by providing for the raw plant material to be continually blended during the irradiating step. Multi-pass radiation with the material being turned or blended between each pass results in uniform radiation of the raw cotton.

Irradiation of the raw plant material forms an irradiated product which is subsequently guided to a micronizing step. Micronizing of the irradiated product is carried out by a micronizing mill, preferably a jet classifying mill such as a model 30 Roto-Jet manufactured by Fluid Energy A1-Jet Company. The jet mill is operated using an air flow of 1500–2000 CFM at 120 psi. This is a high speed grinding mill with an integral, independently driven dynamic classifier producing a narrow size distribution. Although size of the micronized irradiated product may vary depending on the ultimate application for the additive, the general particle range is from about 2 microns to about 10 microns for the applications disclosed herein. For friction-reducing additive applications, 99% of the particles will be below 10 microns in average diameter size with a minimal number of additive particles less than 2 microns in diameter and 0% below 1.0 micron. An average particle diameter of 3 to 4 microns is desirable for friction-reducing applications.

Various alternatives and embodiments are contemplated as being within the scope of the following claims particularly pointing out and distinctly claiming the subject matter regarded as the invention.

I claim:

1. A method for preparing a multifunctional additive from a raw cotton plant material comprising the steps of:
    irradiating the raw cotton plant material with an electron beam source to form an irradiated product, the raw cotton plant material being continually blended during the irradiating step; and
    micronizing the irradiated product.

2. A method according to claim 1 wherein, prior to the irradiating step, a granulating step is included wherein the raw cotton plant material is reduced to a first average diameter size.

3. A method according to claim 2 wherein the granulating step reduces the first average diameter size to about a ⅛ inch to a ¼ inch diameter size.

4. A method according to claim 1 wherein, during the irradiating step, the electron beam source delivers a dosage of about 30 megaRads to about 100 megaRads to the raw cotton plant material.

5. A method according to claim 1 wherein, during the irradiating step, the electron beam source delivers a dosage of about 80 megaRads to about 100 megaRads to the raw cotton plant material.

6. A method according to claim 5 wherein the radiation dosage is applied in multiple low level dosages.

7. A method according to claim 6 wherein the low level dosage comprises about 2.5 megaRads.

8. A method according to claim 6 wherein the material is mixed or blended during the irradiating step.

9. A method according to claim 1 wherein the micronizing step is carried out with a jet classifying mill.

10. A method according to claim 1 wherein the micronizing step reduces a second average diameter size of the irradiated product to about 3 microns to about 4 microns with 99% of the second average diameter sizes below 10 microns.

11. A multifunctional additive prepared from a raw cotton plant material according to the method of claim 1.

12. An additive useful in reducing friction, being used as an anti-misting composition and as a talc substitute, comprising a raw cotton plant material having been subjected to irradiation by an electron beam, the raw cotton plant material being continually blended during the irradiation, the raw cotton plant material subsequently micronized to form an additive with a reduced diameter.

13. An additive according to claim 12 wherein the raw cotton plant material has been subjected to a dosage of about 30 megaRads to about 100 megaRads.

14. An additive according to claim 12 wherein the raw cotton plant material has been subjected to a dosage of about 80 megaRads to about 100 megaRads.

15. An additive according to claim 12 wherein the reduced diameter is about 3 microns to about 4 microns on average with 99% of the reduced diameters below 10 microns.

16. An additive useful in reducing friction, comprising a plant-based biopolymer of raw cotton with an irradiation-induced rearranged structure, the plant-based biopolymer of raw cotton formed into a particulate material having an average diameter size of about 2 microns to about 10 microns.

17. An additive according to claim 16 wherein the average diameter size is about 3 microns to about 4 microns with 99% of the particle diameter sizes below 10 microns.

18. A method of reducing a coefficient of friction in a substance selected from the group comprising a lubricant/grease or cosmetic formulation comprising the step of mixing a friction-reducing additive prepared according to claim 1 with the substance in a sufficient amount to reduce the coefficient of friction of the substance.

* * * * *